United States Patent
Ming et al.

(10) Patent No.: US 10,227,495 B2
(45) Date of Patent: Mar. 12, 2019

(54) BIOCIDAL BIOPOLYMER COATINGS

(71) Applicant: Georgia Southern Research and Service Foundation, Inc., Statesboro, GA (US)

(72) Inventors: Weihua Ming, Statesboro, GA (US); Jie Zhao, Statesboro, GA (US); Wei Ye, Statesboro, GA (US)

(73) Assignee: Georgia Southern Research and Service Foundation, Statesboro, GA (US)

( * ) Notice: Subject to any disclaimer, the term of this patent is extended or adjusted under 35 U.S.C. 154(b) by 0 days.

(21) Appl. No.: 15/664,824

(22) Filed: Jul. 31, 2017

(65) Prior Publication Data
US 2018/0030284 A1  Feb. 1, 2018

Related U.S. Application Data

(60) Provisional application No. 62/368,673, filed on Jul. 29, 2016.

(51) Int. Cl.
| | | |
|---|---|---|
| *C09D 5/14* | (2006.01) | |
| *C09D 175/04* | (2006.01) | |
| *A01N 37/12* | (2006.01) | |
| *C09D 4/00* | (2006.01) | |
| *A01N 47/12* | (2006.01) | |
| *A01N 25/10* | (2006.01) | |
| *C08G 18/36* | (2006.01) | |
| *C08G 18/28* | (2006.01) | |

(52) U.S. Cl.
CPC .............. *C09D 5/14* (2013.01); *A01N 25/10* (2013.01); *A01N 37/12* (2013.01); *A01N 47/12* (2013.01); *C08G 18/2875* (2013.01); *C08G 18/2885* (2013.01); *C08G 18/36* (2013.01); *C09D 4/00* (2013.01); *C09D 175/04* (2013.01)

(58) Field of Classification Search
CPC ........................ C08G 18/36; C08G 18/2875; C08G 18/2885; C09D 4/00; C09D 5/14; C09D 175/04; A01N 25/10; A01N 47/12; A01N 37/12; A01N 33/12
USPC ....................................................... 526/208
See application file for complete search history.

(56) References Cited

U.S. PATENT DOCUMENTS

2011/0293540 A1 * 12/2011 Musa .................... C08F 226/06
424/49

OTHER PUBLICATIONS

Bakhshi, et al., "Polyurethane Coatings Derived from 1,2,3-Triazole-Functionalized Soybean Oil-Based Polyols: Studying their Physical, Mechanical, Thermal, and Biological Properties", Macromolecules 46, 2013, 7777-7788.
Bakhshi, et al., "Synthesis and characterization of antibacterial polyurethane coatings from quaternary ammonium salts functionalized soybean oil based polyols", Materials Science and Engineering C, 2012, 12 pages.

(Continued)

*Primary Examiner* — William K Cheung
(74) *Attorney, Agent, or Firm* — Meunier Carlin & Curfman LLC

(57) ABSTRACT

Disclosed herein are biopolymer-based biocidal coatings. The coatings have excellent antimicrobial and antifungal properties, and retain their activity over substantially prolonged periods of time.

20 Claims, 1 Drawing Sheet

(56) References Cited

OTHER PUBLICATIONS

Bakhshi, et al., "Synthesis and evaluation of antibacterial polyurethane coatings made from soybean oil functionalized with dimethylphenylammonium iodide and hydroxyl groups", J of Biomed. Mat. Research A, 101A, 2013, 1599-1611.

Lee, et al., "Antimicrobial edible defatted soybean meal-based films incorporating the lactoperoxidase system", LWT—Food Science and Technology 54, 2013, 42e50.

Xia, et al., "Antibacterial Soybean-Oil-Based Cationic Polyurethane Coatings Prepared from Different Amino Polyols", ChemSusChem 2012, 5, 2221-2227.

Yagci, et al., "Self-stratifying antimicrobial polyurethane coatings", Progress in Organic Coatings 72, 2011, 305-314.

Zhao, et al., "Dual-Functional Antifogging/Antimicrobial Polymer Coating", ACS Appl. Mater. Interfaces 8, 2016, 8737-8742.

Zhao, et al., "Self-Stratified Antimicrobial Acrylic Coatings via One-Step UV Curing", ACS Appl. Mater. Interfaces 7, 2015, 18467-18472.

\* cited by examiner

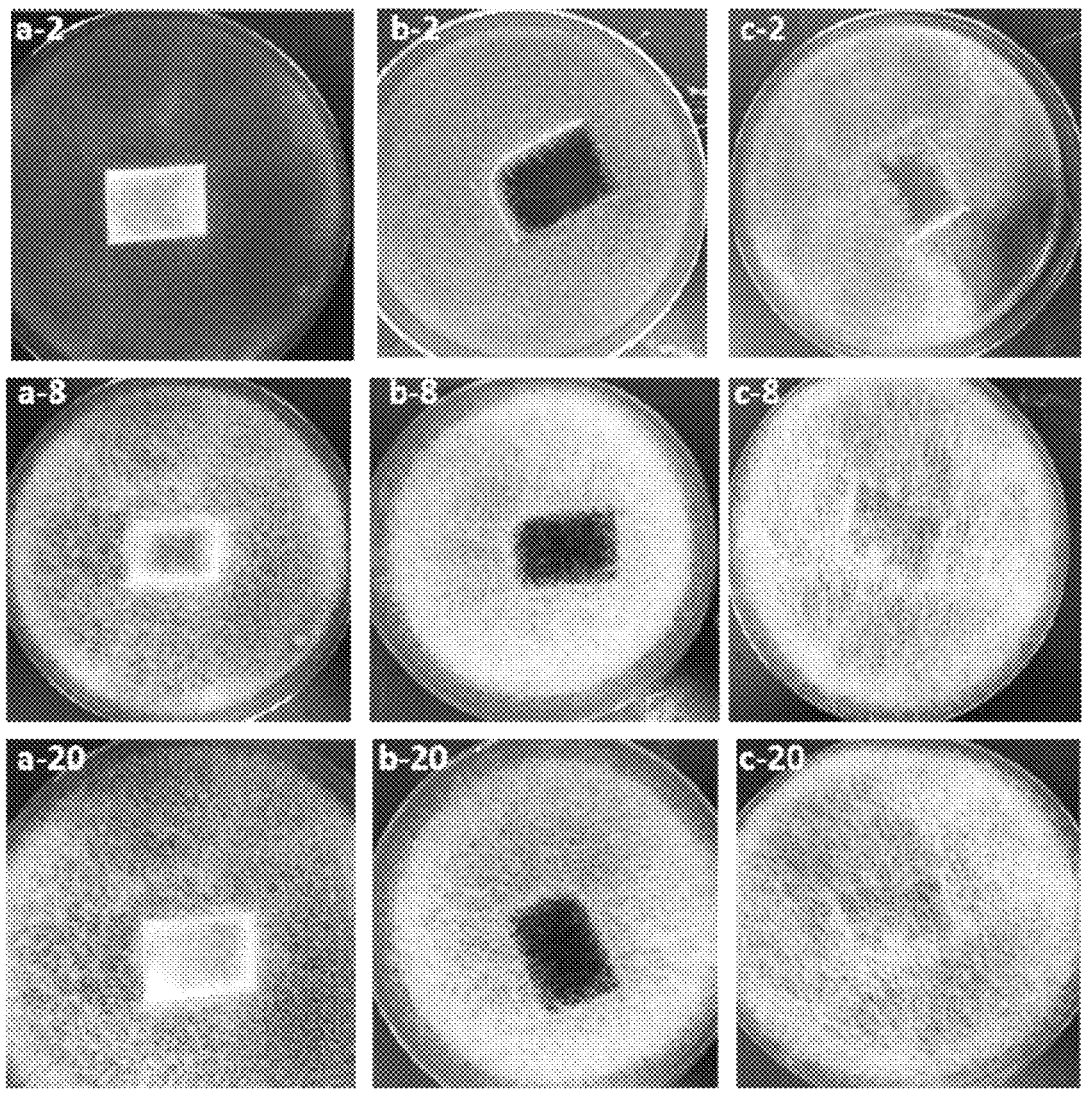

BIOCIDAL BIOPOLYMER COATINGS

CROSS REFERENCE TO RELATED APPLICATION

This application claims the benefit of U.S. Provisional Application 62/368,673, filed on Jul. 29, 2016, the contents of which are hereby incorporated in its entirety.

FIELD OF THE INVENTION

The invention is directed to coatings derived from biomaterials with antimicrobial and antifungal properties.

BACKGROUND

There has been great demand for high-performance antimicrobial and antifungal coating. Commercially available biocidal coatings are made primarily from petrochemicals and involve the use of free biocides. As the biocide leeches into the environment from the coating, biocidal activity is decreased. The release of the biocide also presents ecological concerns, and can accelerate the development of resistant organisms.

Recently, coatings derived from naturally occurring oils incorporating a biocidal component have been reported. However, there remains a need for coatings with enhanced and/or prolonged biocidal activity, addressing on or more of the above concerns.

SUMMARY

Disclosed herein are coatings including crosslinked triglycerides which incorporate a biocidal component. The coatings can be obtained from naturally occurring triglycerides and oils, which may be crosslinked and covalently linked with one or more biocidal components. The coatings exhibit highly potent antimicrobial and antifungal activity over a prolonged period of time, and do not release biocidal compounds into the environment.

The details of one or more embodiments are set forth in the descriptions below. Other features, objects, and advantages will be apparent from the description and from the claims.

BRIEF DESCRIPTION OF THE FIGURES

FIG. 1 includes a depiction of the biocidal activity of coatings of the instant invention in comparison with a commercial fungicide against *R. stolonifera* spore.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Unless stated to the contrary, a chemical formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The term "alkyl" as used herein is a branched, unbranched, or cyclic hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. An alkyl group which contains no double or triple carbon-carbon bonds is designated a saturated alkyl group, whereas an alkyl group having one or more such bonds is designated an unsaturated alkyl group. Unsaturated alkyl groups having a double bond can be designated alkenyl groups, and unsaturated alkyl groups having a triple bond can be designated alkynyl groups. Unless specified to the contrary, the term alkyl embraces both saturated and unsaturated groups.

As used herein, the term (meth)acrylic acid encompasses both acrylic acids and methacrylic acids. The same applies to derivational suffixes, for instance, (meth)acrylate. As used herein, the term "vinyl" refers to a functional group having carbon-carbon double, wherein neither of the carbon atoms is directly bonded to a carbonyl, thiocarbonyl, nitrile, or imine.

As used herein, the term triglyceride refers to a tri-ester of glycerol and three carboxylic acid, wherein each acid contains at least six carbon atoms. Unless specified to the contrary, triglyceride embraces both saturated triglycerides, wherein none of the three carboxylic acids possess any double or triple carbon-carbon bonds, and unsaturated triglycerides, in which at least one of the three carboxylic acids includes at least one olefinic or acetylenic bonds.

Disclosed herein are biocidal coatings of a crosslinked triglyceride/oil incorporating a quaternary ammonium salt within the coating network. The quaternary ammonium salt can be covalently bound to the triglycerides in the network. The quaternary ammonium salt can incorporated into the biocidal coating using a compound of Formula (1):

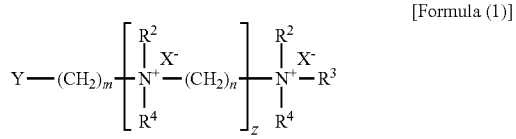

[Formula (1)]

wherein
  z is any integer;
  n is in each instance independently selected from 1-20, for instance, 3-10, 3-5, or 5-10;
  m is selected 1-20, for instance, 2-20, 2-10, 2-5, 3-10, 3-5, or 5-10;
  X is a monovalent anion;
  $R^2$ and $R^4$ are independently selected from $C_{1\text{-}20}$ alkyl, and may together form a ring;
  $R^3$ is $C_{8\text{-}20}$ alkyl; and
  Y represents a reactive functional group.

Suitable monovalent anions for X include F, Cl, Br, I, $NO_3$, $HCO_3$, OAc, OMs, OTs, $HSO_4$, or $H_2PO_3$. Although in some instances the coating can incorporate oligomeric quaternary ammonium groups (i.e., z=1-10, 1-5, 2-5, or 1, 2, 3, 4, 5, 6, 7, 8, 9, or 10), in other cases z will be 0.

In some embodiments, Y can be a nucleophilic functional group such as hydroxyl, amino, thiol, carboxyl and the like. In other embodiments, Y can be an olefinic functional group such as vinyl or (meth)acrylate.

In certain embodiments, $R^2$ and $R^4$ are each an unsubstituted $C_{1\text{-}20}$ alkyl group, and in certain embodiments can be independently selected from $C_{1\text{-}4}$ alkyl. The $C_{1\text{-}4}$ alkyl can be unsubstituted, for instance methyl, ethyl, isopropyl, n-propyl, n-butyl, isobutyl, t-butyl, and sec-butyl. In some cases, either $R^2$ or $R^4$ are benzyl or alkyl substituted benzyl. In other cases $R^2$ and $R^4$ can together form a ring, for instance a pyrrolidinium, piperdinium, morpholinium, piperazinium, or diazapinium ring.

In some embodiments $R^3$ is an unsubstituted $C_{10\text{-}20}$ alkyl, preferably a linear $C_{10\text{-}20}$ alkyl group, or a linear $C_{10\text{-}15}$ alkyl group. Specific unsubstituted $R^3$ groups include decyl, undecyl, dodecyl, pentadecyl, hexadecyl and the like.

In some embodiments, m can be 2, 3, 4, 5, or 6, preferably 2.

In certain embodiments, the biocidal coating can be obtained using a quaternary ammonium salt of Formula (1a):

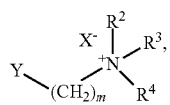

[Formula (1a)]

wherein Y, X, m, $R^2$, $R^3$, and $R^4$ are as defined for the compound of Formula (1). In some embodiments, Y is (meth)acrylate, i.e., a compound of Formula (1b):

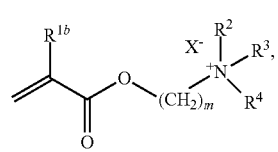

[Formula (1b)]

Wherein X, m, $R^2$, $R^3$, and $R^4$ are as defined for the compound of Formula (1), and $R^{1b}$ is hydrogen or $C_{1\text{-}6}$ alkyl, preferably hydrogen or methyl. In other preferred embodiments, Y is hydroxyl.

The compound of Formula (1) can be combined with the functionalized triglyceride or oil in an amount from 0.5-20% by weight relative to the functionalized triglyceride or oil, for instance from 1-20% by weight, from 1-15% by weight, from 1-10% by weight, from 2-15% by weight, from 2-10% by weight, from 4-10% by weight, from 6-10% by weight, from 5-15% by weight, from 5-20% by weight, or from 10-20% by weight. In some instances, the compound can be present in an amount of at least 0.5% by weight, at least 1% by weight, at least 2% by weight, at least 3% by weight, at least 4% by weight, at least 5% by weight, at least 6% by weight, at least 7% by weight, at least 8% by weight, at least 9% by weight, or at least 10% by weight.

The crosslinked triglyceride/oil can include an oxidized triglyceride or oil. Exemplary oxidized triglycerides/oils include hydroxylated triglycerides/oils, dihydroxylated triglycerides/oils, and epoxidized triglycerides/oils. Although the addition of water across an olefin is not formally an oxidation, as used herein the term embraces such compounds. Oxidized triglycerides can be obtained by oxidative hydroxylation, dihydroxylation, or epoxidation of triglycerides having elements of unsaturation, e.g., double bonds, preferably at least two double bonds. Although the coatings can contain a single, oxidized triglyceride, the coating can also include a mixture of different oxidized triglycerides, for instance obtained by oxidizing an oil. Exemplary oils that may be used include plant oils, animal oils, or algae oils. For instance, the oil can be one or more of beef tallow, butter, lard, sesame seed oil, coconut oil, rapeseed oil, palm oil, beef tallow, fish oil (for instance cod, shark, salmon, or sardine), soy bean oil, canola oil, sunflower oil, camelina oil, safflower oil, rice bran oil, corn oil, olive oil, peanut oil, kernel oil, cottonseed oil, tung oil, castor oil, linseed oil, and colza oil.

Each oil contains a characteristic mix of saturated and unsaturated (enoic, dienoic, trienoic, etc) triglycerides. The relative amount (weight percent) of certain unsaturated triglycerides for some of the oils above is listed in the below table:

|  | Enoic | | | | Dienoic | Trienoic |
| --- | --- | --- | --- | --- | --- | --- |
| Oil | $<C_{16}$ | $C_{16}$ | $C_{18}$ | $>C_{18}$ | $C_{18}$ | $C_{18}$ |
| Beef tallow | 0.5 | 2-3 | 9-42 | 0.3 | 2 | |
| Butter | 1-2 | 2-5 | 2-29 | 0.2-1.5 | 3 | |
| Coconut | | | 5-8 | 0-1 | 1-3 | |
| Corn | | 1-2 | 0-50 | 0-2 | 34-56 | |
| Cottonseed | | | 3-44 | 0-1 | 34-55 | |
| Lard | 0.2 | 2-5 | 1-51 | 2-3 | 3-8 | |

-continued

| Oil | Enoic | | | | Dienoic | Trienoic |
|---|---|---|---|---|---|---|
| | <$C_{16}$ | $C_{16}$ | $C_{18}$ | >$C_{18}$ | $C_{18}$ | $C_{18}$ |
| Olive | | 1-3 | 3-86 | 0-3 | 4-22 | |
| Palm | | | 0-52 | | 2-11 | |
| Palm Kernal | | 0-1 | 0-18 | | 1-2 | |
| Peanut | | 1-2 | 9-66 | | 17-38 | |
| Soybean | | 0-1 | 2-34 | | 50-60 | 2-10 |
| | | | | $C_{20}$ 25-32 | >$C_{20}$ 10-20 | |
| Codliver | 0-2 | 10-20 | 5-31 | | 8-29 | 45-67 |
| Linseed | | | 9-29 | | 8-29 | 45-67 |
| Tung | | | 4-13 | | 8-15 | 78-82 |

Exemplary triglycerides found in some of oils listed above include those incorporating one or more of crotonic acid, myristoleic, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, tetra-unsaturated fatty acids, stearidonic acid, arachidonic acid, eicosatetraenoic acid, adrenic acid, bosseopentaenoic acid, eicosapentaenoic acid, ozubondo acid, sardine acid, tetracosanolpentaenoic acid, docosahexaenoic acid, or herring acid.

In some preferred embodiments, the biocidal coating includes a crosslinked oxidized soybean oil. Natural soybean oil includes triglycerides incorporating alpha-linolenic acid, linoleic acid, and oleic acid, among others. Other preferred oils include camelina oil, which is characterized by a high content of unsaturated triglycerides.

Oxidized triglycerides can be characterized by their oxygen content. For instance, epoxidized triglycerides and oils useful for the coatings of the present invention can have an oxirane oxygen content of at least 2%, at least 3%, at least 4%, at least 5%, at least 6%, at least 7%, at least 8%, at least 9%, or at least 10%, by weight. Epoxidized triglycerides and oils useful for the coatings of the present invention can have an oxirane oxygen content from 1-15%, from 1-10%, from 2-10%, from 3-10%, from 4-10%, from 5-10%, from 2.5-7.5%, from 5-15% by weight, from 7.5-15%, from 5-12.5%, or from 7.5-12.5%. Oxirane content can be determined using the American Oil Chemists' Society (AOCS) method Cd 9-57.

Hydroxylated triglycerides can be characterized according to their hydroxyl value, which can be determined using AOCS method Cd 13-60. Hydroxylated triglycerides and oils useful for the coatings of the present invention can have a hydroxyl value of at least 100 mg KOH/g, at least 150 mg KOH/g, at least 200 mg KOH/g, at least 250 mg KOH/g, at least 300 mg KOH/g, at least 350 mg KOH/g, at least 400 mg KOH/g, at least 450 mg KOH/g, at least 500 mg KOH/g, at least 600 mg KOH/g, at least 700 mg KOH/g, at least 800 mg KOH/g, at least 900 mg KOH/g, or at least 1000 mg KOH/g. Hydroxylated triglycerides and oils useful for the coatings of the present invention can have a hydroxyl value between 100-1,000 mg KOH/g, between 100-1,000 mg KOH/g, between 250-1,000 mg KOH/g, between 500-1,000 mg KOH/g, between 750-1,000 mg KOH/g, or between 250-750 mg KOH/g.

Triglycerides and oils can be further characterized by the iodine value, which measures the remaining amount of olefinic bonds after epoxidation or hydroxylation. Iodine value can be determined using AOCS method Cd 1d-92. Oxidized triglycerides and oils useful for the coatings of the present invention can have an iodine value no greater than 10, no greater than 9, no greater than 8, no greater than 7, no greater than 6, no greater than 5, no greater than 4, no greater than 3, no greater than 2, or no greater than 1. Oxidized triglycerides and oils useful for the coatings of the present invention can have an iodine value between 0.5-10, between 0.5-7.5, between 0.5-5, between 1-5, between 1-2.5, between 0.5-1, between 1-2, between 2.5-7.5, or between 2.5-5.

The biocidal resins can be obtained from crosslinking functionalized triglycerides and oils. Functionalized triglycerides include those that have at least 2, 3, 4, 5, 6, 7, 8, 9, or 10 crosslinkable functional groups per molecule. Crosslinkable functional groups include those crosslinkable via radical mediated reactions. Exemplary groups include olefins such as alkenyls, alkynyls, and (meth)acrylate esters. Crosslinkable functional groups also include those crosslinkable via nucleophilic reactions. Exemplary groups alcohols, thiols, carboxyls, and amines. Functionalized triglycerides and oils can be obtained by ring-opening reactions of epoxidized triglycerides, by nucleophilic reactions with hydroxylated triglycerides (e.g., esterification and etherification), or by other chemical processes known by those of skill in the art.

Olefinic groups can be incorporated into an epoxidized soybean oil by oxirane-ring opening with a nucleophile bearing one or more olefinic groups. As used herein, the term "functionalized, epoxidized triglyceride" refers to the product of this reaction (triglyceride may refer to a single triglyceride, or a mixture of triglycerides as found in an oil). Ring opening with a meth(acrylic) acid compound will install meth(acrylate) groups, and ring opening with a compound such as allyl alcohol will install vinyl groups. The hydroxyl value of the resulting compound can used to assess the level of incorporation for the polymerizable functional group, as each epoxide opened necessary results in the formation of a single hydroxyl group as well. The hydroxyl value for a functionalized, epoxidized triglyceride or oil can be from 10-1,000 mg KOH/g, 50-1,000 mg KOH/g, 100-1,000 mg KOH/g, 10-500 mg KOH/g, 50-500 mg KOH/g, 100-500 mg KOH/g, 100-300 mg KOH/g, or 100-250 mg KOH/g. In some instances, the (meth)acrylated epoxidized triglyceride can be characterized by an oxirane content no greater than 10%, no greater than 9%, no greater than 8%, no greater than 7%, no greater than 6%, no greater than 5%, no greater than 4%, no greater than 3%, no greater than 2%, or no greater than 1% by weight. The (meth)acrylated epoxidized triglyceride can be characterized by an iodine value no greater than 10, no greater than 9, no greater than 8, no greater than 7, no greater than 6, no greater than 5, no greater than 4, no greater than 3, no greater than 2, or no greater than 1 by weight.

When the functionalized triglyceride include olefinic groups, the crosslinking reaction may be carried out using irradiation. Suitable irradiation conditions include UV irradiation, e.g., at 365 nm, 400 W, for a period of time sufficient to form the coating. For instance, the mixture may be irradiated for at least 5 seconds, at least 10 seconds, at least 15 seconds, at least 20 seconds, at least 30 seconds, at least 1 minute, at least 2 minutes, at least 5 minutes, at least 10 minutes, at least 30 minutes, at least 60 minutes, at least 120 minutes, at least 240 minutes, or at least 360 minutes, depending on the type of coating desired. Radical based crosslinking reactions may be further carried out in the presence of another di-olefinic crosslinker, such as divinylbenzene or a related compound, in an amount from 0.1-10% by weight, from 1-10% by weight, from 1-7.5% by weight, from 2.5-7.5% by weight, from 2.5-5% by weight, from 1-3% by weight, from 2-3% by weight, or from 1-2% by weight, from 5-15% by weight, from 5-20% by weight, or from 10-20% by weight.

When the functionalized triglycerides includes nucleophilic groups (alcohols, amines, carboxyls, or thiols), the crosslinking reaction may be carried out crosslinking agents such as polyisocyanates, e.g., a diisocyanate. As used herein, a polyisocyanate refers to a chemical compound having two or more isocyanate functional groups and a diisocyanate refers to a chemical compound having two isocyanate functional groups. Exemplary diisocyanates include as toluene diisocyanate, methylenediphenyl diisocyanate, 4,4-diphenylmethane diisocyanate, isophorone diisocyanate, and hexamethylene diisocyanate. Suitable diisocyanates include MDI, IPDI, TDI, and HDI. Suitable polyisocyanates are available under various tradenames such as Easaqua, Bayhydur, Basonat, Coronate, Desmodur, Crelan, and the like. The di- or polyisocyanate can be added in an excess amount relative to the total hydroxyl content in the oxidized triglyceride and compound of Formula (1). A catalyst may also be added, for instance tin compounds, bismuth compound, nickel compounds, zinc compounds, and tertiary amines. The mixture may be heated to a temperature greater than 40° C., 50° C., 60° C., 70° C., or 80° C., for period of time of at least 2 hours, at least 3 hours, at least 4 hours, at least 5 hours, at least 6 hours, at least 7 hours, at least 8 hours, at least 9 hours, or at least 10 hours to yield the coating.

The above components can be combined in a solvent prior to crosslinking. The solvent may cast upon a surface prior to crosslinking to provide a biocidal coating on the surface. Suitable solvents include organic solvents that dissolve the components and are relatively volatile, for instance, solvents having a boiling point less than 80° C.

In some embodiments, the crosslinking and incorporation steps are carried out concurrently. For instance, if the functionalized triglyceride and compound of Formula (1) both contain polymerizable olefins, the crosslinking and incorporation step can be achieved at the same time by irradiating a mixture of the functionalized triglyceride and compound of Formula (1). When the functionalized triglyceride and compound of Formula (1) both contain nucleophilic functional groups, the crosslinking and incorporation step can be achieved at the same time by combining the functionalized triglyceride and compound of Formula (1) with a polyisocyanate or diisocyanate.

Although in most embodiments the biocidal coating is obtained from a concurrent crosslinking/incorporation protocol, in other cases the crosslinking and incorporation can be conducted sequentially. For instance, the triglyceride may first be crosslinked, and then in a subsequent step, the compound of Formula (1) may be incorporated. In other cases, the compound of Formula (1) may be incorporated into the functionalized triglyceride, which may then be crosslinked. Sequential reactions may be achieved using separate reaction steps (i.e., crosslinking in the absence of the compound of Formula 1), or by employing orthogonal functional groups (i.e., when the compound of Formula (1) includes Y=hydroxyl, crosslinking a (meth)acrylate hydroxylated triglyceride under radical conditions, and then adding a polyisocyanate).

The functionalized triglyceride can be a compound of Formula (2):

Formula (2)

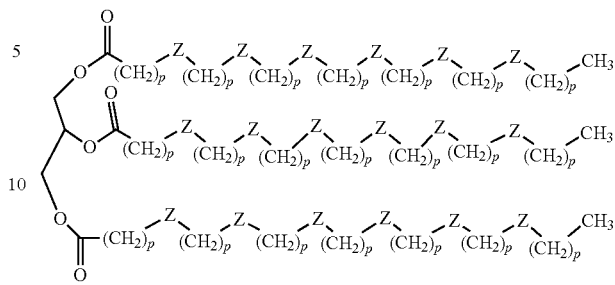

wherein p is independently selected from 1-20, 1-10, 1-8, or 1-6, and Z is independently selected from a chemical bond, or a group of the formula:

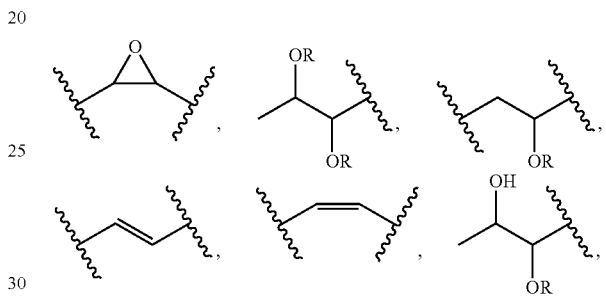

wherein R is independently selected from hydrogen, $C_3$-$C_{12}$ alkenyl, $C_3$-$C_{12}$ alkynyl, or a (meth)acrylate group of the formula:

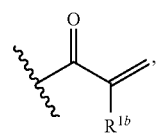

wherein $R^{1b}$ is hydrogen or $C_{1-7}$ alkyl, and
when Z is

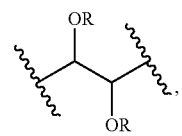

wherein adjacent R groups may together form an anhydride, providing that at least two Z groups are independently selected from:

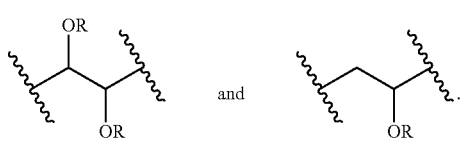

In some embodiments, when Z is:

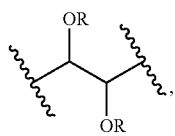

one R can be hydrogen and the other is a (meth)acrylate, preferably in which $R^{1b}$ is hydrogen or methyl. When Z is:

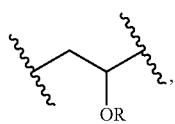

R can be $C_3$-$C_{12}$ alkenyl, $C_3$-$C_{12}$ alkynyl, or (meth)acrylate, as described above, preferably in which $R^{1b}$ is hydrogen or methyl. In other cases, R can be hydrogen.

In certain embodiments, the functionalized triglyceride can be a compound of Formula (2a)

Formula (2a)

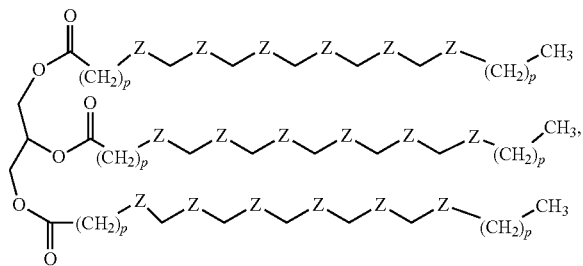

wherein p and Z are as defined above.

The skilled person will appreciate that an oxidized oil, as it contains a plurality of oxidized triglycerides, will contain a variety of different compounds having a structure of Formula (2) or (2a).

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Synthesis of Quaternary Ammonium Salts

Meth(Acrylate) Functionalized Ammonium Compound 2-(N,N-dimethyl-N-undecylammonium ethyl methacrylate bromide (Ac-QAC) was synthesized by reacting 2-(di-methylamino)ethyl methacrylate (DMAEMA) and 1-bromoundecane (BU). DMAEMA (2.2 mmol) and BU (2 mmol) were first dissolved in 10 mL of acetonitrile; the mixture was purged with N2 for 20 min and reacted at 50° C. for 12 h under magnetic stirring. After that, the solvent was removed and the residue was dried under vacuum oven at 40° C. for 24 h to obtain Ac-QAC.

Hydroxyl Functionalized Ammonium Compound

11-[(N,N)-dimethyl-N-undecylammonium] undecan-1-ol (QAC-OH) was synthesized from N,N-dimethylundecyl amine (DMUA) and 11-bromo-1-undecanol (BUO). 4 mmol DMUA and 4.2 mmol BUO were first dissolved in 12 mL mixture of propanol and methanol (3:1 v/v) in a 25-mL round bottom flask, and refluxed at 80° C. for 90 min. After that, QAC-OH was obtained by precipitating the reaction mixture in ethyl ether twice and drying in a vacuum oven overnight.

For comparative purpose, 3-[(N,N)-dimethyl-N-undecylammonium] propan-1-ol (QAC-OH-2) which has a much shorter spacer, —$(CH_2)_3$— between the quaternary ammonium moiety and the OH group than QAC-OH, —$(CH_2)_{11}$—, was synthesized by reacting 3-dimethyl-amino-1-propanol (DMAP, 2.2 mmol) with BU (2 mmol).

Example 2: AESO Biocidal Coating

Two grams of acrylated epoxidized soybean oil (AESO) was combined with Ac-QAC (0, 2, 4, 6, or 8% by weight relative to AESO) divinyl benzene (0.1 g, 5% by weight relative to AESO), and initiator 2-hydroxy-4-(2-hydroxy-ethoxy)-2-methylpropiophenone (HHMP, 0.01 g) in 5 mL of chloroform. The mixture was then purged with $N_2$ for 5 min to remove oxygen, and spun-coated onto cleaned aluminium panels at 800 rpm for 15 s. The liquid mixture was then UV-cured for 15 s on a UV apparatus (Fusion UV Curing System, F300S, 365 nm, 400 W) to obtain cross-linked coatings.

Quantitative evaluation of antimicrobial activity of coatings prepared above against E. coli and S. epidermidis was examined through the conventional test of bacterial activity, in which the reduction of the number of viable bacterial cells ($\log_{10}$ scale) as colony forming units (CFU) within 24 h was recorded (Table 1). The coatings based on AESO, containing 6-8 wt % Ac-QAC by UV curing, demonstrated excellent antimicrobial property: 5-log reduction (99.999%) against both gram-positive S. epidermidis and gram-negative E. coli.

TABLE 1

Bacterial log reduction after 24 h of incubation of $10^5$ bacteria with 2.0 × 2.0 $cm^2$ coating films based on AESO.

| Sample | Ac-QAC content with respect to AESO (wt %) | E. coli | S. epidermidis |
|---|---|---|---|
| Control [a] | 0 | 0.7 | 0.5 |
| AESO-2 | 2 | 3.0 | 3.1 |
| AESO-4 | 4 | 3.5 | 4.5 |

TABLE 1-continued

Bacterial log reduction after 24 h of incubation of
$10^5$ bacteria with 2.0 × 2.0 cm$^2$ coating films based on AESO.

| Sample | Ac-QAC content with respect to AESO (wt %) | E. coli | S. epidermidis |
|---|---|---|---|
| AESO-6 | 6 | 4.5 | 5.0 |
| AESO-8 | 8 | 5.0 | 5.0 |

[a] The control was an AESO-based coating without QAC.

To confirm that the QAC (ammonium compound) moieties cannot leach out of the coating, the coatings were subjected to a zone of inhibition test in the lawns of *S. epidermidis*. No bacterial inhibition zone was observed around the representative samples (AESO-6 and AESO-8) against *S. epidermidis*, showing that no biocidal QAC species was leached out from the cross-linked coatings. The zone of inhibition test also revealed that the antimicrobial activity in the coatings was completely based on contact killing, not due to the release of any antimicrobial agent.

Example 3: HSO Biocidal Coating

Antimicrobial coatings were prepared from a mixture of hydroxylated soybean oil (HSO), QAC-OH or QAC-OH-2, and a polyisocyanate cross-linker via thermal curing. In detail, the reactive mixture contained 1.0 g of HSO, 0.63 g of a commercially available polyisocyanate cross-linker (Easaqua XL 600, 10% excess of NCO with respect to the OH content), varying amounts of QAC-OH or QAC-OH-2 (0-8.0 wt % with respect to the total amount of the HSO and polyisocyanate), and 0.5 wt % of dibutyltin dilaurate used as the catalyst. The mixtures were dissolved in chloroform (2 mL) to obtain uniform solutions, followed by spin coating onto clean aluminum panels at 300 rpm for 20 s. The liquid coating mixture was then thermally cured at 60° C. for 2-8 h to obtain smooth SBO-based polyurethane coatings.

TABLE 2

Bacterial log reduction after 24-h incubation - with initial bacterial concentration of $10^5$ bacteria/mL, treated with QAC-OH-HSO-XL600 coatings (2.2 × 2.2 cm$^2$).

| Sample | QAC-OH content with respect to HSO (wt %) | E. coli | S. epidermidis |
|---|---|---|---|
| Control [a] | 0 | 0.5 | 0.8 |
| Q1-HSO-2 | 2 | 3.0 | 3.6 |
| Q1-HSO-4 | 4 | 4.3 | 4.0 |
| Q1-HSO-8 | 8 | 5.0 | 5.0 |

[a] The control was a HSO-based PU coating without QAC-OH.

As shown in Table 2, as the QAC-OH content was increased to 2 wt %, more than 99.9% (3-log reduction) of bacteria, both *E. coli* and *S. epidermidis*, were killed, indicating excellent antimicrobial effect of this coating. Incorporation of 8 wt % of QAC-OH into the PU coating led to total kill against both bacteria. Coatings using another polyisocyanate cross-linker, EASAQUA XD803, appeared to have similar antimicrobial property, in spite of the different NCO contents in EASAQUA XD803 and EASAQUA XL600.

As shown in Table 3, the QAC-OH-2-containing PU coatings also demonstrated very good antimicrobial property against both bacteria. Their bacteria-killing efficiency did appear to be slightly less than their QAC-OH counterparts, very likely the consequence of the longer spacer in QAC-OH that may lead to greater surface segregation of bacteria-killing QAC at the coating surface.

TABLE 3

Bacterial log reduction after 24-h incubation - with initial bacterial concentration of $10^5$ bacteria/mL, treated with QAC-OH-2-HSO-XL600 coatings (2.2 × 2.2 cm$^2$).

| Sample | QAC-OH-2 content with respect to HSO (wt %) | E. coli | S. epidermidis |
|---|---|---|---|
| Control [a] | 0 | 0.5 | 0.8 |
| Q2-HSO-2 | 2 | 3.0 | 3.2 |
| Q2-HSO-4 | 4 | 3.5 | 3.8 |
| Q2-HSO-8 | 8 | 4.5 | 5.0 |

[a] The control was a HSO-based PU coating without QAC-OH-2.

Example 4: Antifungal Activity of HSO Biocidal Coating

*R. stolonifer* (black bread mold) was selected as a model fungus to challenge the antifungal activity of HSO-based antimicrobial PU coating, together with a PU coating containing a commercial fungicide (analogous to PolyPhase 663). *R. stolonifer* was cultured on potato dextrose agar (PDA) for 3-4 days to allow sporulation. Spores were then collected by gently rubbing the plate surface with a sterile cotton swab, followed by immersion in 1 mL of sterile DI water. All coatings to be challenged were cut into squares and put on the PDA surface with no air bubble between PDA and the coating. The spore suspension was then transferred onto the PDA and coating surface by gently drawing lines via a sterile cotton swab. The plates were sealed and incubated under room temperature for different periods of time.

After 2-day incubation, there appeared to be some difference in fungal growth in the three coatings examined: there was more fungal growth on the control coating (containing a commercial fungicide) and the coating with QAC-OH-2 than that with QAC-OH (b-2, FIG. 1), indicating that the QAC-OH-containing coating showed stronger fungus-inhibiting effect than the other two. Longer incubation time (8 and 20 days) revealed more significant difference: for the control sample and QAC-OH-2-containing coating, the fungal growth was much more substantial, as indicated by the spreading of hyphae on the sample surface, than on the QAC-OH-containing coating. The fungal coverage after 20 days on these two samples (a-20 & c-20, FIG. 1) was almost full, and even mycelium had already formed. In contrast, only light hyphae growth along the edge of the sample was observed for the QAC-OH-containing coating (b-8 & b-20, FIG. 1), clearly pointing to its much stronger antifungal activity than the other two.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

5. The biocidal coating according to claim 1, wherein $R^2$ and $R^4$ are independently selected from $C_{1-4}$ alkyl.

6. The biocidal coating according to claim 1, wherein $R^3$ a linear $C_{10-15}$ alkyl group.

7. The biocidal coating according to claim 1, wherein the functionalized triglyceride comprises an oxidized oil.

8. The biocidal coating according to claim 7, wherein the oxidized oil comprises a plant oil, an animal oil, an algae oil, or a mixture thereof.

9. The biocidal coating according to claim 8, wherein the oxidized oil comprises beef tallow, butter, lard, sesame seed oil, coconut oil, rapeseed oil palm oil, beef tallow, fish oil, soy bean oil, canola oil, sunflower oil, camelina oil, safflower oil, rice bran oil, corn oil, olive oil, peanut oil, kernel oil, cottonseed oil, tung oil, castor oil, linseed oil, colza oil, or a mixture thereof.

10. The biocidal coating according to claim 1, wherein the functionalized triglyceride comprises an epoxidized, (meth)acrylated triglyceride.

11. The biocidal coating according to claim 1, wherein the functionalized triglyceride comprises a compound having the formula:

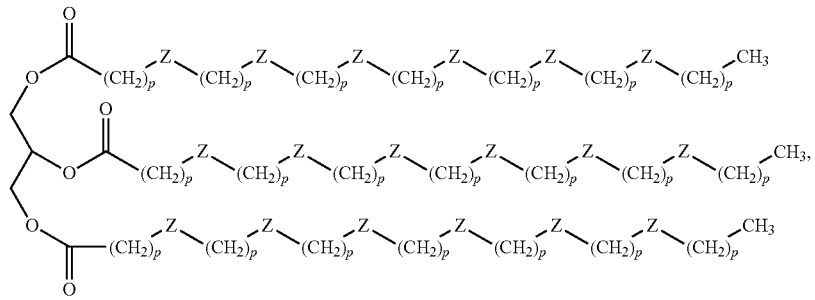

What is claimed is:

1. A biocidal coating, prepared by a process comprising:
a) crosslinking a functionalized triglyceride; and
b) covalently incorporating a compound of Formula (2) into the functionalized triglyceride:

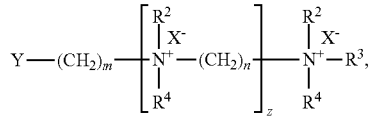

Formula (2)

wherein:
z is any integer;
n is in each instance independently selected from 1-20;
m is selected 1-20;
X is a monovalent anion;
$R^2$ and $R^4$ are independently selected from $C_{1-20}$ alkyl, and may together form a ring;
$R^3$ is $C_{8-20}$ alkyl; and
Y is a reactive functional group.

2. The coating according to claim 1, wherein Y is a functional group selected from the group consisting of hydroxyl, amino, thiol, carboxyl, (meth)acrylate, vinyl, and alkynyl.

3. The coating according to claim 1, wherein the crosslinking and incorporation steps are conducted concurrently.

4. The coating according to claim 1, wherein z is 0.

wherein p is independently selected from 1-20, and Z is independently selected from a chemical bond, or a group of the formula:

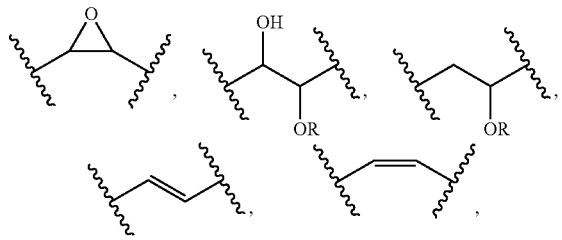

wherein R is independently selected from hydrogen, $C_3$-$C_{12}$ alkenyl, $C_3$-$C_{12}$ alkynyl, or a (meth)acrylate group of the formula:

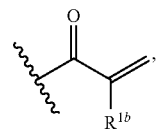

wherein $R^{1b}$ is hydrogen or $C_{1-7}$ alkyl,
wherein at least two Z groups are independently selected from:

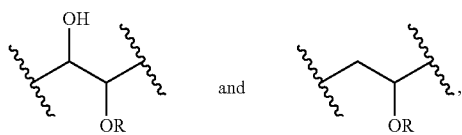

and wherein are least two R groups are $C_3$-$C_{12}$ alkenyl, $C_3$-$C_{12}$ alkynyl, or have the formula:

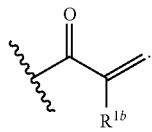

12. The biocidal coating according to claim 10, wherein Y comprises a (meth)acrylate group.

13. The biocidal coating according to claim 12, obtained by the process of preparing a mixture of the functionalized triglyceride and the compound of Formula (1), and irradiating the mixture to give the biocidal coating.

14. The biocidal coating according to claim 13, wherein the compound of Formula (1) is present in an amount of 2-10% by weight relative to the functionalized triglyceride.

15. The biocidal coating according to claim 14, wherein the mixture further comprises an additional crosslinker in an amount from 2-10% by weight relative to the functionalized triglyceride.

16. The biocidal coating according to claim 1, wherein the functionalized triglyceride comprises hydroxylated triglyceride.

17. The biocidal coating according to claim 16, wherein Y is hydroxyl.

18. The biocidal coating according to claim 17, obtained by the process of preparing a mixture of the hydroxylated triglyceride and the compound of Formula (2), and combining the mixture with a polyisocyanate to give the biocidal coating.

19. The biocidal coating according to claim 18, wherein the compound of Formula (2) is present in an amount of 2-10% by weight relative to the hydroxylated triglyceride.

20. The biocidal coating according to claim 18, wherein the polyisocyanate is present in an amount to give 5-20% excess NCO groups relative to hydroxyl content.

* * * * *